US00PP33285P3

(12) United States Plant Patent
Serrador

(10) Patent No.: US PP33,285 P3
(45) Date of Patent: Jul. 27, 2021

(54) STRAWBERRY PLANT NAMED 'A13-07'

(50) Latin Name: ***Fragaria* x *ananassa Duch.***
Varietal Denomination: A13-07

(71) Applicant: MASIA CISCAR S.A., Lepe (ES)

(72) Inventor: Enrique Masiá Serrador, Huelva (ES)

(73) Assignee: MASIÁ CISCAR S.A., Lepe (ES)

( * ) Notice: Subject to any disclaimer, the term of this patent is extended or adjusted under 35 U.S.C. 154(b) by 0 days.

(21) Appl. No.: 16/974,159

(22) Filed: Oct. 23, 2020

(65) Prior Publication Data

US 2021/0127536 P1 Apr. 29, 2021

Related U.S. Application Data

(60) Provisional application No. 62/973,792, filed on Oct. 24, 2019.

(51) Int. Cl.
*A01H 6/74* (2018.01)
*A01H 5/08* (2018.01)

(52) U.S. Cl.
USPC ..... Plt./208
CPC ..... *A01H 6/7409* (2018.05)

(58) Field of Classification Search
USPC ..... Plt./208
See application file for complete search history.

*Primary Examiner* — Annette H Para
(74) *Attorney, Agent, or Firm* — Svendsen Legal, LLC

(57) ABSTRACT

A new strawberry plant named 'A13-07' is disclosed, with exceptional yield and flavor characteristics.

4 Drawing Sheets

Genus and species: *Fragaria* x *ananassa* Duch.
Variety denomination: 'A13-07'.

STATEMENT REGARDING FEDERALLY SPONSORED RESEARCH OR DEVELOPMENT

None

BACKGROUND OF THE INVENTION

'A13-07' is a product of a controlled breeding program carried out by the inventor in the Andalucia region of Spain. 'A13-07' was one of several seedlings resulting from an uncontrolled cross made in the year 2014. Mother parent is 'A13-26' (U.S. Plant Pat. No. 32,137) and father parent is unknown. The seeds resulting from the uncontrolled cross were germinated indoors and the resulting seedling was transplanted to the trial seedling field. 'A13-07' was selected in the Andalucia region of Spain in the year 2015 based on observations of its fruiting characteristics. In 2016, 'A13-07' was asexually propagated by rooting stolons and was expanded to 30 plants which were planted in replicated trials in the Andalucia region of Spain. The plants were observed and evaluated, and the next year they were expanded for further observation and evaluation. The breeders of 'A13-07' have sold the variety commercially under the trade name SHYRA WB™. Contrast is made with SPENDOR™ (U.S. Plant Pat. No. 17,864 cultivar named 'BG-959') In reference to color of the fruit, 'A13-07' fruit is red orange and 'BG-959' presents a dark red fruit. 'A13-07' produces fruit larger in size (5-7 cm) versus 'BG-959' having medium size fruit (4.5-5.5 cm). Also, comparison is made with strawberry variety 'FRONTERAS' (U.S. Plant Pat. No. 26,709). The plants of 'A13-07' variety produce a more vigorous plant than 'FRONTERAS'. The fruit of 'A13-07' is medium red in color and the fruit of 'FRONTERAS' is bright red. The medium red color and large fruit size of the variety 'A13-07' along with its good organoleptic characteristics makes it a desirable fruit that can be traded in the fruit markets. Throughout several generations of asexual propagation, 'A13-07' has been observed to retain its distinctive characteristics and remain true to type.

BRIEF DESCRIPTION OF THE PHOTOGRAPH

Figure 1:
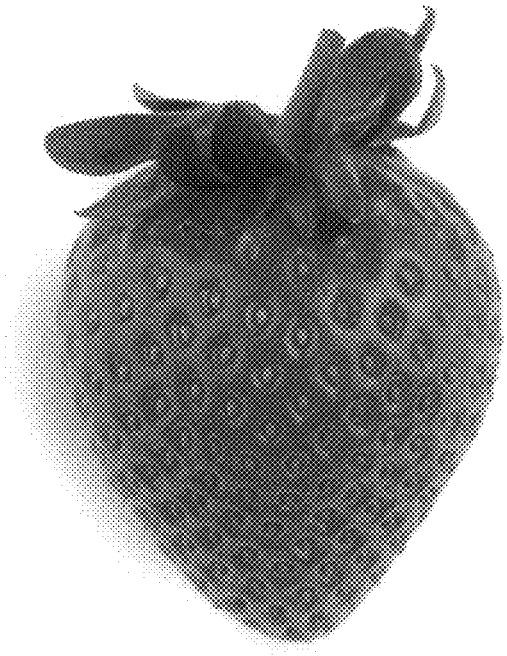
FIG. 1 illustrates a mature strawberry of 'A13-07'.
Figure 2:
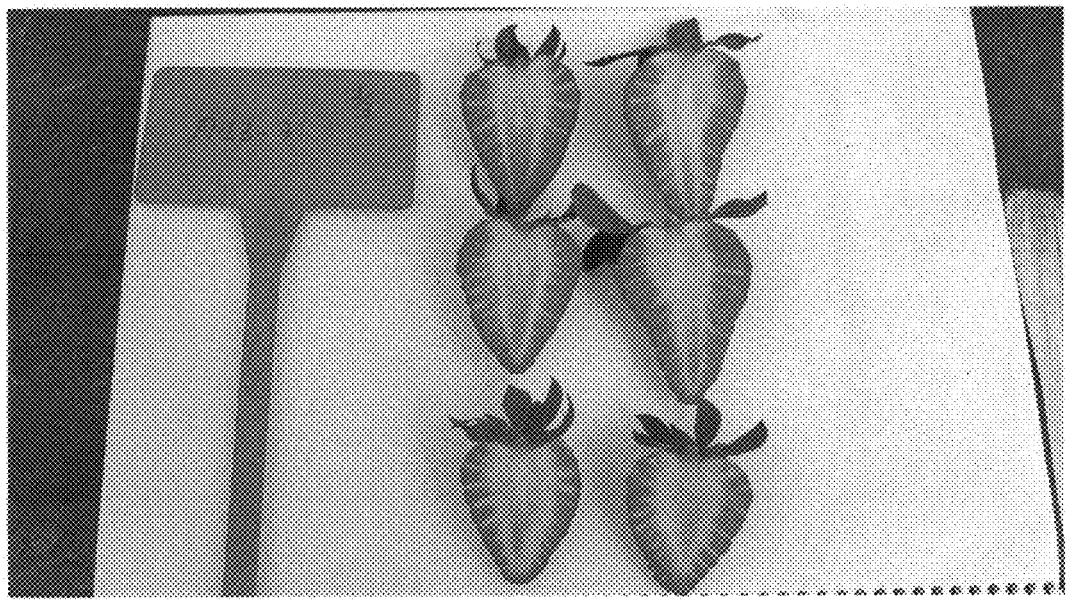
FIG. 2 illustrates cross sections of whole berries of mature strawberries of 'A13-07'.
Figure 3:
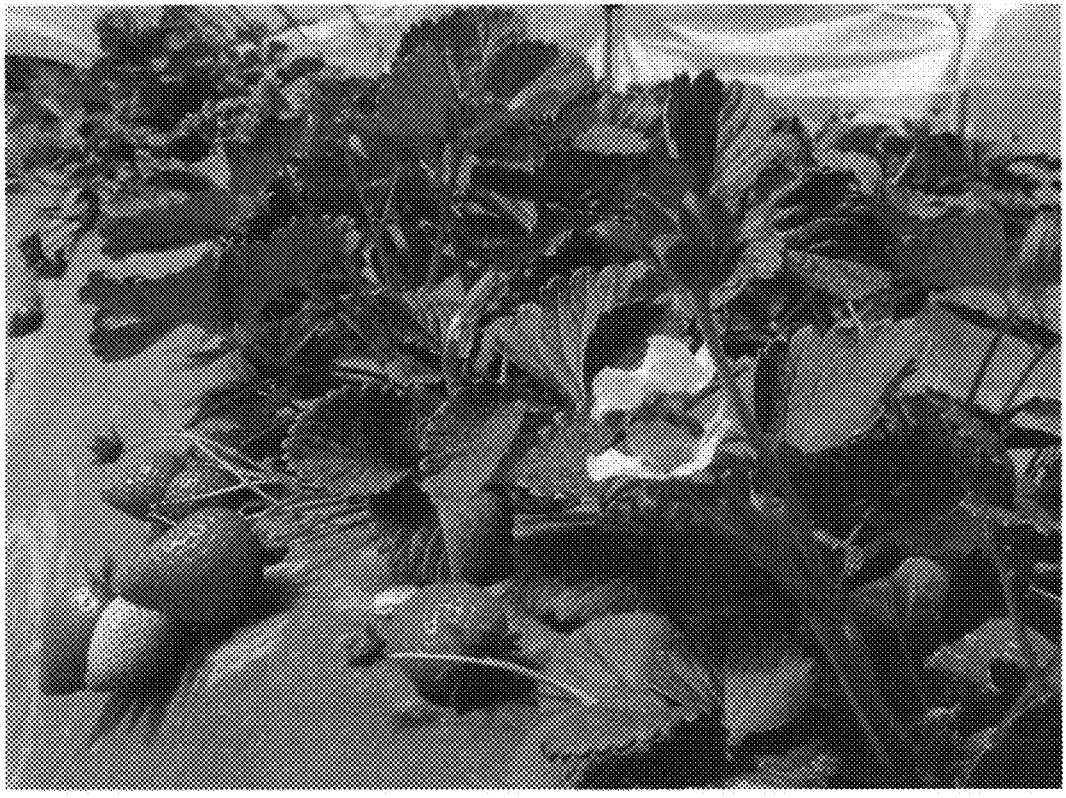
FIG. 3 illustrates 6-month-old plants of 'A13-07' growing in a raised bench system.
Figure 4:
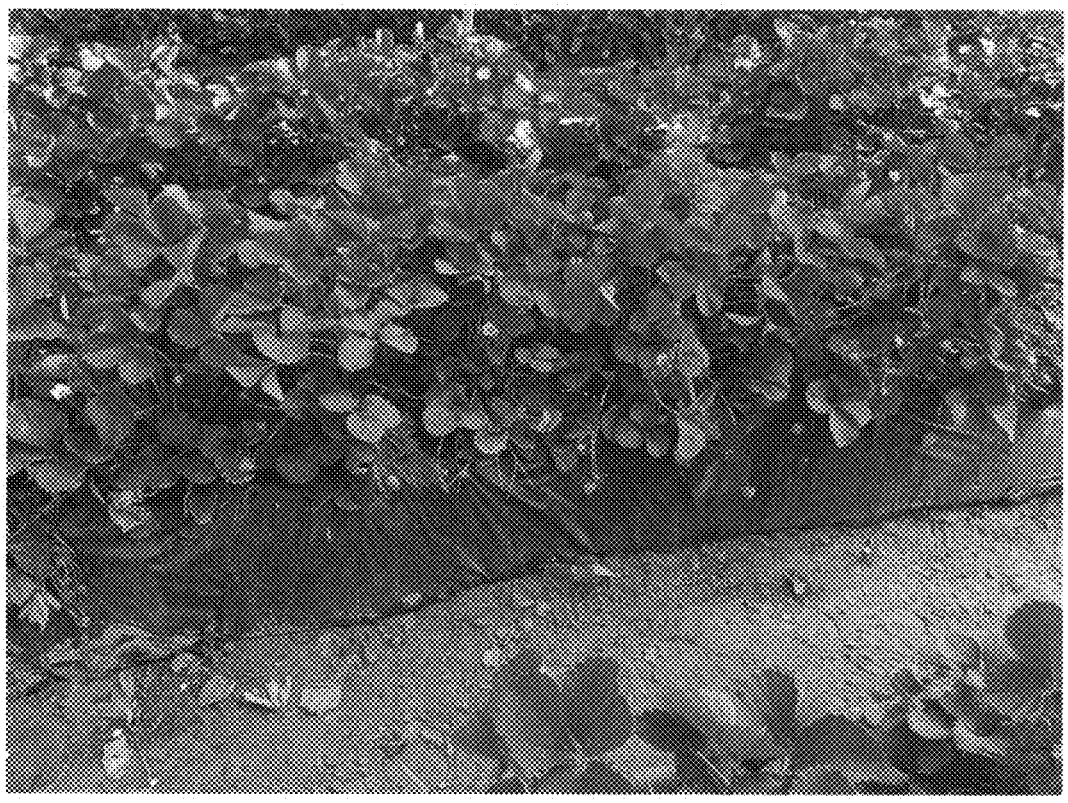
FIG. 4 illustrates immature plants of 'A13-07' growing in a traditional raised bed with black plastic mulch.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is that of a plant age of seven months and is based on observations made during the 2018 and 2019 growing seasons in the Andalucia region of Spain. It should be understood that the characteristics described will vary somewhat depending upon cultural practices and climatic conditions and can vary with location and season. Quantified measurements are expressed as an average of measurements taken from a number of individual plants of the new variety. The measurements of any individual plant or any group of plants, of the new variety may vary from the stated average. Color terminology follows The Royal Horticultural Society Colour Chart, London (R.H.S.) (Sixth Revised Edition, 2015).

General description:
*Ploidy*.—Octoploid.
*Blooming period*.—Very early.
*Plant average height*.—31 cm.
*Plant average width*.—28 cm.
*Plant type*.—Herbaceous fruit producing perennial.
*Plant habit*.—Semi upright, medium density, medium vigor.
*Cold hardiness*.—Not tested in areas where temperatures of 32° F. occur.
*Root description*.—Greyed-yellow group (160) Pale greenish yellow (C).
*Propagation*.—Rooting of stolons.
*Growth rate*.—Medium vigor.
*Stem*.—Acaulescent.

Stolons:
*Anthocyanin*.—Absent to moderate.
*Average length*.—30-40 cm.
*Average diameter*.—4 mm.
*Average number*.—Variable, 30-40.
*Color*.—Yellow-green group (145) Strong yellow green (A).

Foliage description:
*Average leaf length*.—11 cm.
*Average leaf width*.—17 cm.
*Leaf texture* (*both surfaces*).—Moderately soft on both sides.
*Leaf pubescence*.—Medium.
*Leaf division*.—Three leaflets.
*Leaf arrangement*.—Basal.
*Leaf attachment*.—Petiolate.
*Terminal leaflet average length*.—11 cm.
*Terminal leaflet average width*.—8.5 cm.
*Terminal leaflet pubescence density*.—Medium.
*Terminal leaflet texture* (*both surfaces*).—Moderately soft on both sides.
*Leaflet shape*.—Broadly ovate to rounded.
*Leaflet margins*.—Serrate to Crenate.
*Leaflet base*.—Obtuse.
*Leaflet apex*.—Round.
*Leaflet venation*.—Pinnate.
*Leaflet color*.—Upper surface Green group (143) Strong yellow green (B) and Lower surface Green group (143) Moderate yellow green (D).

Petiole:
*Average length*.—19 cm.
*Average diameter*.—4 mm.
*Pubescence*.—Low to medium.
*Pubescence density*.—Moderate.
*Pose of hairs*.—Slightly outwards.
*Texture*.—Moderately soft.
*Anthocyanin*.—Absent.
*Color*.—Yellow-green group (144) Light yellow green (D).

Petiolule:
*Average length*.—Terminal leaflet 10 mm, Lateral leaflet 5 mm.
*Average diameter*.—2 mm.
*Color*.—Yellow-green group (144) Light yellow green (D).

Stipule:
*Average length*.—25 mm.
*Average width*.—12 mm.
*Color*.—Yellow-green group (145) Light yellow green (C).

Flower description:
*Average size* (*diameter*).—41 mm.
*Average number of flowers*.—3-6 flowers per cluster.
*Inflorescence*.—Above.
*Time of flowering* (50% *of plants at first flower*).—Very early.

Sepal:
*Average length*.—15 mm.
*Average diameter*.—8.7 mm.
*Texture* (*both surfaces*).—Both surfaces partially soft.
*Color*.—Yellow-green group (144) Strong yellow green (B).
*Sepal position*.—Upwards.

Petals:
*Average number*.—5.
*Average length*.—10 mm.
*Average width*.—10.5 mm.
*Texture*.—Soft.
*Color*.—White Group (NN155) White (C).

Peduncle:
*Average length*.—35-45 cm.
*Average diameter*.—4 mm.
*Color*.—Yellow-green group (144) Light yellow green (D).

Pedicel:
*Average length*.—7-10 cm.
*Average diameter*.—2 mm.
*Color*.—Yellow-green group (144) Light yellow green (D).
*Stigma color*.—Yellow-green group (153) Strong yellow (D).
*Style color*.—Yellow-green group (153) Strong yellow (D).
*Stamens average length*.—1.5 mm.
*Stamens color*.—Yellow-green group (153) Strong greenish yellow (C).

Fruit description:
*Shape*.—Reniform, conical.
*Time of ripening* (50% *of plants with first ripe fruit*).—Early.
*Average length of fruit*.—5-7 cm.
*Average width of fruit*.—3-5 cm.
*Weight of primary fruit*.—35-50 grams.
*Weight of secondary and tertiary fruit*.—15-35 grams.
*Fruit cavity*.—Small to medium (4 mm-20 mm).
*Surface*.—Even or slightly uneven.
*Glossiness*.—Medium.
*External color* (*skin*).—Orange-red group (33) Vivid reddish orange (A).
*Internal color* (*skin*).—Orange-red group (33) vivid reddish Orange (B).
*Evenness of color of skin*.—Even or very slightly uneven.
*Sweetness*.—Brix 8.
*Firmness*.—Firm, 509 on penetrometer.
*Yield*.—Average of 959.46g per plant.
*Achene*.—Shady side Orange-red group (32) Strong reddish orange (B) and Sunny side Orange-red group (32) Strong Yellowish pink (C).
*Achenes*.—Level with surface.

Disease and pest resistance: 'A13-07' variety is sensitive to aphids among which is *Aphis gossypii*. On the other hand, the mildew of the powdery mildew (*Podosphaera aphanis*) that causes ash disease must be controlled.

The invention claimed is:

1. A new and distinct strawberry plant as shown and described herein.

* * * * *